United States Patent
Teng et al.

(10) Patent No.: US 7,754,751 B2
(45) Date of Patent: Jul. 13, 2010

(54) PREFERENTIAL INHIBITION OF RELEASE OF PRO-INFLAMMATORY CYTOKINES

(75) Inventors: Che-Ming Teng, Taipei (TW); Jih-Hwa Guh, Taipei (TW); Shiow-Lin Pan, Taipei (TW); Sheng-Chu Kuo, Taichung (TW); Fang-Yu Lee, Tachia Taichung (TW)

(73) Assignee: Yung Shin Pharmaceutical Ind. Co., Ltd., Tachia, Taichung (TW)

( * ) Notice: Subject to any disclaimer, the term of this patent is extended or adjusted under 35 U.S.C. 154(b) by 1520 days.

(21) Appl. No.: 11/080,384

(22) Filed: Mar. 15, 2005

(65) Prior Publication Data
US 2005/0215613 A1 Sep. 29, 2005

Related U.S. Application Data

(60) Provisional application No. 60/553,302, filed on Mar. 15, 2004.

(51) Int. Cl.
*A01N 43/56* (2006.01)
*C07D 231/10* (2006.01)
*C07D 231/12* (2006.01)

(52) U.S. Cl. ............ 514/403; 514/406; 548/373.1
(58) Field of Classification Search ............ 514/403, 514/406; 548/373.1
See application file for complete search history.

(56) References Cited

U.S. PATENT DOCUMENTS

| 6,162,819 A | 12/2000 | Schindler et al. |
| 6,943,186 B2 | 9/2005 | Teng |

FOREIGN PATENT DOCUMENTS

| EP | 1331223 A | 7/2003 |
| WO | WO 03/068754 A | 8/2003 |
| WO | WO 03/090870 A | 12/2003 |
| WO | WO 2004/091648 | 10/2004 |

OTHER PUBLICATIONS

Iqbal et al. Expert Opinion on Emerging Drugs. 2002, vol. 7, No. 1, pp. 111-139.*
Lien et al. Journal of Medicinal Chemistry, 2002. vol. 45, No. 23, pp. 4947-4949.*
Ferrero and Torres, "Prolonged exposure to YC-1 induces apoptosis in adrenomedullary endothelial and chromaffin cells through a cGMP-independent mechanism" Neuropharmacology 41:895-906, 2001.
Flamigni et al, "Control of survival of proliferating L1210 cells by soluble guanylate cyclase and p44/42 mitogen-activated protein kinase modulators", Biochemical Pharmacology 62:319-328, 2001.
Lee et al., "Synthesis of 1-Benzyl-3-(5'-hydroxymethyl-2'-furyl)indazole Analogues as Novel Antiplatelet Agents", J. Med. Chem., 44:3746-3749, 2001.
Lien et al., "1-Benzyl-3-(5'-hydroxymethyl-2'-furyl)-indazole (YC-1) Derivatives as Novel Inhibitors Against Sodium Nitroprusside-Induced Apoptosis", Journal of Medicinal Chemistry, vol. 45, No. 23, 4979-4949, 2002.
Yu et al. "Inhibition of Platelet Function by A02131.1, a Novel Inhibitor of cGMP-Specific Phosphodiesterase, In Vitro and In Vivo", Blood vol. 87, No. 9, pp. 3758-3767, 1996.

* cited by examiner

*Primary Examiner*—Sreeni Padmanabhan
*Assistant Examiner*—Samira Jean-Louis
(74) *Attorney, Agent, or Firm*—Howrey LLP; Viola T. Kung

(57) ABSTRACT

A method for preferentially inhibiting release of pro-inflammatory cytokines over release of anti-inflammatory cytokines using a fused pyrazolyl compound of formula (I):

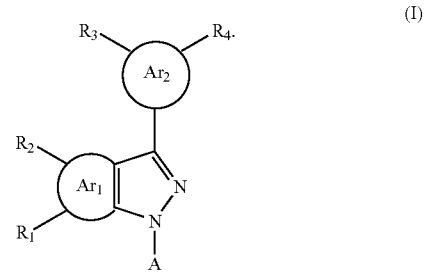

A is R or

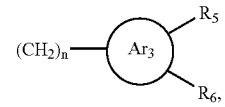

in which R is H, alkyl, aryl, cyclyl, heteroaryl, or heterocyclyl; each of $Ar_1$, $Ar_2$, and $Ar_3$, independently, is phenyl, thienyl, furyl, or pyrrolyl; each of $R_1$, $R_2$, $R_3$, $R_4$, $R_5$, and $R_6$, independently, is R', nitro, halogen, —C(O)—OR', —C(O)—SR', —C(O)—NR'R", —$(CH_2)_m$OR', —$(CH_2)_m$SR', —$(CH_2)_m$NR'R", —$(CH_2)_m$CN, —$(CH_2)_m$C(O)—OR', —$(CH_2)_m$C(O)H, or $R_1$ and $R_2$ together, $R_3$ and $R_4$ together, or $R_5$ and $R_6$ together are —O(CH2)$_n$O—, in which each of R' and R", independently, is H, alkyl, cyclyl, aryl, heteroaryl, heterocyclyl; and m is 0, 1, 2, 3, 4, 5, or 6; and n is 1, 2, or 3. This invention also covers a method of inhibiting activity of NF-κB with such a compound.

11 Claims, No Drawings

PREFERENTIAL INHIBITION OF RELEASE OF PRO-INFLAMMATORY CYTOKINES

RELATED APPLICATIONS

This application claims priority to U.S. provisional application No. 60/553,302, filed on Mar. 15, 2004, the content of which is incorporated herein by reference.

BACKGROUND

Cytokines are a unique family of growth factors. They act as endogenous mediators that coordinate inflammatory signaling (Romagnani S., *Ann Allergy Asthma Immunol.* 2000, 85: 9-21).

Pro-inflammatory cytokines (e.g., TNF-α and interleukins 1β, 2, and 8), produced predominantly by activated macrophages, trigger inflammatory response to exogenous pathogens. However, their overproduction is detrimental to vital organs. Anti-inflammatory cytokines (e.g., interleukins 4 and 10) cease or attenuate inflammatory progression so as to retain the functions of vital organs (Taniguchi et al., *Crit. Care Med.* 1999, 27: 1262-1264; and Kasai et al., *Res. Commun. Mol. Pathol. Pharmacol.* 1997, 98: 34-4220).

Production of pro-inflammatory and anti-inflammatory cytokines is stringently regulated via complicated mechanisms. Imbalanced production of the two cytokines results in many diseases, e.g., arthritis, renal disease, bone abnormalities, asthma, cancer, sepsis, neurodegeneration, neutrophilic alveolitis, hepatitis, ischemia/reperfiision, and inflammatory bowel disease (Taniguchi et al., *Crit. Care Med.* 1999, 27: 1262-1264; and Kasai et al., *Re,s Commun. Mol. Pathol. Pharmacol.* 1997, 98: 34-42).

NF-κB is a transcriptional factor that mediates cytokine release and plays a key role in modulating inflammatory response. It is a potential target for treating diseases, such as rheumatoid arthritis, inflammatory bowel disease, multiple sclerosis psoriasis, asthma, septic shock, autoimmune diseases (e.g., systemic lupus erythromatus), neurodegeneration, atherosclerosis, oncogenesis, ataxia telangiectasia, lung diseases (e.g., ARDS, systemic inflammatory response syndrome, respiratory viral infections, occupational and environmental lung disease, cystic fibrosis, idiopathic pulmonary fibrosis, primary pulmonary hypertension), HIV, and influenza (Kristman J W., et al., *Chest* 2000, 117: 1482-1487; and Baldwin, A S. Jr., *Annu. Rev. Immunol.* 1996, 14: 649-683).

SUMMARY

This invention is based on surprising discoveries that a fused pyrazolyl compound preferentially inhibits the release of pro-inflammatory cytokines over anti-inflammatory cytokines, and that this compound also inhibits the activity of NF-κB.

Thus, one aspect of this invention relates to a method for preferentially inhibiting the release of four or more pro-inflammatory cytokines over the release of one or more anti-inflammatory cytokines in a subject. The method includes administering to a subject an effective amount of one or more of the fused pyrazolyl compounds of formula (I):

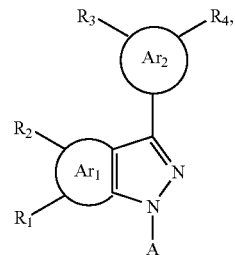

in which A is R or

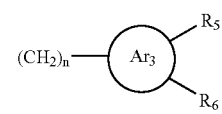

(referred to as "$(CH_2)_n Ar_3(R_5)(R_6)$" hereinafter), in which R is H, alkyl, aryl, cyclyl, heteroaryl, or heterocyclyl; each of $Ar_1$, $Ar_2$, and $Ar_3$, independently, is phenyl, thienyl, furyl, or pyrrolyl; each of $R_1$, $R_2$, $R_3 R_4$, $R_5$, and $R_6$, independently, is R', nitro, halogen, —C(O)—OR', —C(O)—SR', —C(O)—NR'R", —$(CH_2)_m$OR', —$(CH_2)_m$SR', —$(CH_2)_m$NR'R", —$(CH_2)_m$CN, —$(CH_2)_m$C(O)—OR', —$(CH_2)_m$C(O)H, or $R_1$ and $R_2$ together, $R_3$ and $R_4$ together, or $R_5$ and $R_6$ together are —O$(CH_2)_m$O—, in which each of R' and R", independently, is H, alkyl, cyclyl, aryl, heteroaryl, heterocyclyl; and m is 0, 1, 2, 3, 4, 5, or 6; and n is 1, 2, or 3.

Referring to formula (I), a subset of the fused pyrazolyl compounds are those in which $Ar_2$ is 5'-furyl and A is $(CH_2)_n Ar_3(R_5)(R_6)$. In some compounds, $Ar_1$ is thienyl or phenyl, $Ar_3$ is phenyl, n is 1, or $R_3$ is $CH_2OH$ or $CO_2H$ and substituted at position 2 of furyl.

Another subset of the fused pyrazolyl compounds are those in which $Ar_2$ is 5'-furyl and A is H. In some compounds, $R_3$ is $CO_2CH_3$ and substituted at position 2 of furyl, $Ar_1$ is phenyl, or each of $R_1$ and $R_2$ is H.

In a preferred embodiment of the above-described method, the fused pyrazolyl compounds preferentially inhibit release of five or more pro-inflammatory cytokines over release of two or more anti-inflammatory cytokines in a subject. The pro-infammatory cytokines can be interleukin 1β, interleukin 6, interleukin 8, interferon γ and TNF-α; and the anti-inflammatory cytokines can be interleukin 4 and interleukin 10.

Another aspect of this invention relates to a method for inhibiting activity of NF-κB by administering to a subject an effective amount of one or more of fused pyrazolyl compounds.

As the compounds of formula (I) preferentially inhibit pro-inflammatory cytokines over anti-inflammatory cytokines and inhibit the activity of NF-κB, they are useful in treating diseases that relate to imbalanced production of pro- and anti-inflamrmatory cytokines or excessive activity of NF-κB.

The term "alkyl" herein refers to a straight or branched hydrocarbon, containing 1-10 carbon atoms. Examples of alkyl groups include, but are not limited to, methyl, ethyl, n-propyl, i-propyl, n-butyl, i-butyl, and t-butyl.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl.

The term "cyclyl" refers to saturated and partially unsaturated cyclic hydrocarbon group having 3 to 12 carbons. Examples of cyclyl groups include, but are not limited to, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having one or more heteroatoms (such as O, N, or S). Examples of heteroaryl groups include pyridyl, furyl, imidazolyl, benzimidazolyl, pyrimidinyl, thienyl, quinolinyl, indolyl, and thiazolyl. The term "heteroaralkyl" refers to an alkyl group substituted with a heteroaryl group.

The term "heterocyclyl" refers to a nonaromatic 5-8 membered monocyclic, 8-12 membered bicyclic, or 11-14 membered tricyclic ring system having one or more heteroatoms (such as O, N, or S). Examples of heterocyclyl groups include, but are not limited to, piperazinyl, pyrrolidinyl, dioxanyl, morpholinyl, and tetrahydrofuranyl.

Alkyl, cyclyl, heterocyclyl, and aryl mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, heterocyclyl, in which alkyl, alkenyl, alkynyl, alkyloxy, aryl, heteroaryl cyclyl, and heterocyclyl may be further substituted.

Set forth below are examples of the fused pyrazolyl compounds which can be used to practice the method of this invention:

Compound 1

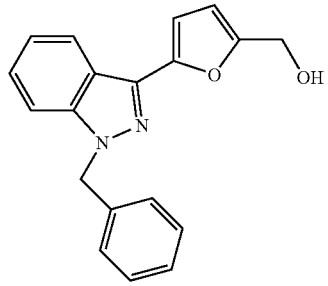

Compound 2

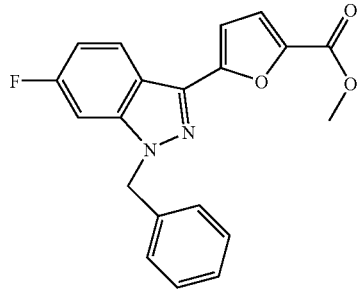

Compound 3

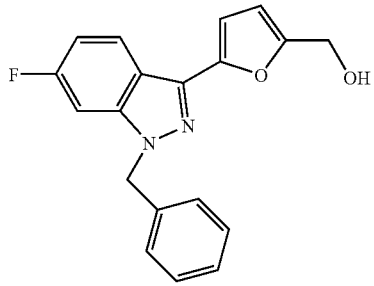

Compound 4

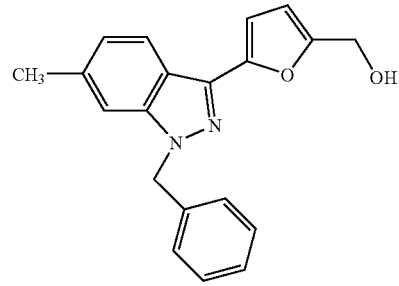

Compound 5

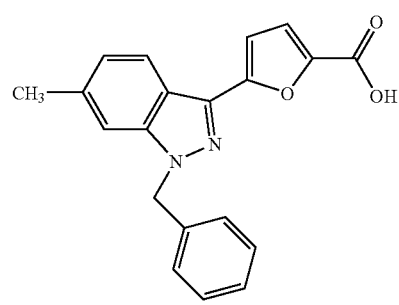

Compound 6

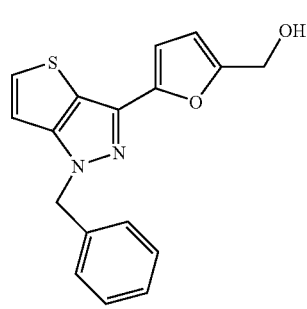

Compound 7

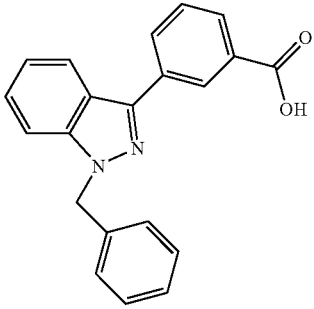

Compound 8

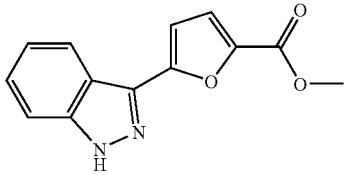

-continued

Compound 9

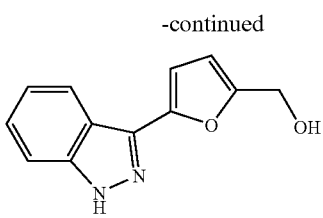

The fused pyrazolyl compounds described above include the compounds themselves, as well as their salts and their prodrugs, if applicable. Such a salt, for example, can be formed between a negatively charged substituent (e.g., carboxylate) on a fused pyrazolyl compound and a cation. Suitable cations include, but are not limited to, sodium ion, potassium ion, magnesium ion, calcium ion, and an ammonium cation such as tetramethylammonium ion. Likewise, a positively charged substituent (e.g., ammonium) can form a salt with a negatively charged counterion. Suitable counterions include, but are not limited to, chloride, bromide, iodide, sulfate, nitrate, phosphate, or acetate. Examples of prodrugs include esters and other pharmaceutically acceptable derivatives, which, upon administration to a subject, are capable of providing the fused pyrazolyl compounds described above (see Goodman and Gilman's, The Pharmacological basis of Therapeutics, 8$^{th}$ ed., McGraw-Hill, Int. Ed. 1992, "Biotransformation of Drugs").

Other features, objects, and advantages of the invention will be apparent from the description and drawings, and from the claims.

DETAILED DESCRIPTION

Any of fused pyrazolyl compounds described in the "Summary" section can be prepared by procedures well known to a skilled person in the art (see, e.g., U.S. Pat. No. 5,574,168 and U.S. Pat. No. 6,162,819). They include the following synthetic route.

An aryl aryl ketone is first prepared by coupling an arylcarbonyl chloride with another aryl compound. Either aryl compound is optionally mono- or multi-substituted. The ketone then reacts with an arylalkylhydrazine (Oanalkyldryazine, hydrazine), the aryl group of which is also optionally mono- or multi-substituted, to form a hydrazone containing three (or two) aryl groups. The hydrazone group is transformed into a fused pyrazolyl core via an alkylene linker, another aryl group is fused at 4-C and 5-C of the pyrazolyl core, and the third aryl group is directly connected to 3-C of the pyrazolyl core. Derivatives of the fused pyrazolyl compound may be obtained by modifying the substituents on any of the aryl groups.

The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the fused pyrazolyl compounds. In addition, various synthetic steps may be performed in an alternate sequence or order to give the desired compounds. Synthetic chemistry transformations and protecting group methodologies (protection and deprotection) useful in synthesizing applicable fused pyrazolyl compounds are known in the art and include, for example, those described in R. Larock, Comprehensive Organic Transformations, VCH Publishers (1989); T. W. Greene and P. G. M. Wuts, Protective Groups in Organic Synthesis, 3$^{rd}$ Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

A fused pyrazolyl compound thus synthesized can be further purified by flash column chromatography, high performance liquid chromatography, or crystallization.

This invention features a method for preferentially inhibiting pro-inflammatory cytokines over anti-inflammatory cytokines. The method includes administering to a subject in need thereof an effective amount of one or more fused pyrazolyl compounds described above and a pharmaceutically acceptable carrier. The term "preferentially inhibiting release of a pro-inflammatory cytokine over release of an anti-inflammatory cytokines" as used herein refers to inhibiting release of a pro-inflammatory cytokine by a compound at a rate at least 3 times that at which release of an anti-inflammatory cytokine is inhibited by the same compound. "An effective amount" is the amount of a fused pyrazolyl compound which, upon administration to a subject in need thereof, is required to confer the above-described inhibitory effect in the subject. Effective amounts may vary, as recognized by those skilled in the art, depending on route of administration, excipient usage, and the possibility of co-usage with other agents.

This invention also features a method for inhibiting the activity of NF-κB. The method includes administering to a subject in need thereof an effective amount of one or more fused pyrazolyl compounds described above and a pharmaceutically acceptable carrier.

To practice the methods of the present invention, a fused pyrazolyl compound can be administered orally, parenterally, by inhalation spray or via an implanted reservoir. The term "parenteral" as used herein includes subcutaneous, intracutaneous, intravenous, intramuscular, intraarticular, intraarterial, intrasynovial, intrastemal, intrathecal, intralesional, and intracranial injection or infusion techniques.

A composition for oral administration can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives, are useful in the preparation of injectables, as are natural pharmaceutically-acceptable oils, such as olive oil or castor oil, especially in their polyoxyethylated versions. These oil solutions of suspensions can also contain a long-chain alcohol diluent or dispersant, or carboxymethyl cellulose or similar dispersing agents.

An inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A carrier in a pharmaceutical composition must be "acceptable" in the sense of being compatible with the active ingredient of the formulation (and preferably, capable of stabilizing it) and not deleterious to the subject to be treated. For example, solubilizing agents, such as cyclodextrins (which form specific, more soluble complexes with fused pyrazolyl compounds), can be utilized as pharmaceutical excipients for delivery of fused pyrazolyl compounds. Examples of other carriers include colloidal silicon dioxide, magnesium stearate, cellulose, sodium lauryl sulfate, and D&C Yellow #10.

A suitable in vitro assay can be used to preliminarily evaluate the efficacy of a fused pyrazolyl compound in preferentially inhibiting pro-inflammatory cytokines over anti-inflammatory cytokines in human peripheral blood mononuclear leukocytes and in inhibiting the activity of NF-κB. In vivo screening can also be performed by following procedures well known in the art. For example, a fused pyrazolyl compound is administered to an animal model (e.g., a mouse) and blood is collected to assess the levels of various cytokines. Based on the results, an appropriate dosage range and administration route can also be determined.

Without further elaboration, it is believed that the above description has adequately enabled the present invention. The following specific examples are, therefore, to be construed as merely illustrative, and not limitative of the remainder of the disclosure in any way whatsoever. All of the publications, including patents, cited herein are hereby incorporated by reference in their entirety.

EXAMPLE 1

Synthesis of 3-(5'-hydroxymethyl-2'-furyl)-1-benzyl-indazol (Compound 1)

(a) Synthesis of 5-methoxycarbonyl-2-furyl phenyl ketone

Anhydrous ferric chloride (0.42 g, 2.6 mmole) and benzoyl chloride (29.6 g, 0.21 mole), were dissolved in $CCl_4$ (40 mL) and added dropwise over 10 min with methyl-2-furoate (25.2 g, 0.20 mmole). The reaction mixture was then heated under reflux for 36 hours, and after cooling was added with water (120 mL). The mixture was stirred for 1 hour and then allowed to sit until it separated into two layers. The water layer and precipitate were extracted with chloroform. The chloroform extract was dried over anhydrous magnesium sulfate and then filtered. The solvent of the filtrate was removed under a reduced pressure; the residue was recrystallized from isopropanol to afford 28.4 g of 5-methoxycarbonyl-2-furyl phenyl ketone in a yield of 65.0%.

mp: 70-73° C.
MS (%), m/z: 230 ($M^+$).
IR (KBr) $\gamma_{max}$: 1720, 1650 $cm^{-1}$ (C=O).
$^1$H-NMR ($CDCl_3$, 200 MHz) δ: 3.86 (3H, s, —$CH_3$), 7.26-7.32 (2H, m, H-3',5'), 7.40-7.65 (3H, m, H-3,4,4'), and 8.05-8.10 (2H, m, H-2', 6').

(b) Synthesis of 1-benzyl-3-(5'-methoxycarbonyl-2'-furyl)indazole

5-Methoxycarbonyl-2-ftiryl phenyl ketone (5.5 g, 0.024 mole) was dissolved in methanol (60 mL), added with benzylhydrazine (9 g, 0.07 mole) and acetic acid (0.5 mL) and then heated under reflux till the reaction was completed. After cooling, the solvent was evaporated. The resultant residue was extracted with chloroform and washed with dilute HCl solution, then water, and then dried over anhydrous magnesium sulfate and filtered. The solvent of the filtrate was removed to give 5-methoxycarbonylfuryl phenyl ketone benzylhydrazone.

A solution of hydrazone thus obtained in dichloromethane (100 mL) was added dropwise to the solution of $Pb(OAc)_4$ (28.2 g, 0.06 mole) in dichloromethane (400 mL). After addition, the mixture was allowed to react at 30±2° C. for 30 min, and $BF_3$-$Et_2O$ (containing 47% of $BF_3$, 122 mL) was added. The mixture was heated under reflux for 30 min and then poured into ice water (1000 mL) to terminate the reaction. The organic layer was separated and washed sequentially with water and 10% sodium carbonate solution, then neutralized by water wash. It was dried over anhydrous magnesium sulfate and was concentrated under vacuum to an oily crude product. Ethanol was then added to the crude product, and the mixture was allowed to precipitate by freeze overnight. The solid precipitate was collected and recrystallized from ethanol to give 3.7 g 1-benzyl-3-(5'-methoxycarbonyl-2'-furyl)indazole in a yield of 47.0% mp: 117-118° C.
MS (%), m/z: 332 ($M^+$).
IR (KBr) $\gamma_{max}$: 1720 $cm^{-1}$ (C=O).
$^1$H-NMR ($CDCl_3$) δ: 3.95 (3H, s, $CH_3$), 5.66 (2H, s, =$NCH_2$—), 7.02 (1H, d, J=3.5 Hz, H-3'), 7.20-7.40 (9H, m, H-5, 6, 7, 4', phenyl), and 8.26 (1H, dd, J=8.1, 1.5 Hz, H-4).

(c) Synthesis of 3-(5'-hydroxymethyl-2'-fuiryl)-1-benzyl-indazol

Calcium borohydride was first prepared by stirring anhydrous calcium chloride (88.8 mg, 0.8 mmole) with sodium borohydride (60 mg, 1.6 mmole) in anhydrous THF (20 mL) for 4 hrs. A 30 mL THF solution containing 88.0 mg 1-benzyl-3-(5'-methoxycarbonyl-2'-furyl)-indazole (0.27 mmole) was then added dropwise to the calcium borohydride solution at 30±2° C. The mixture was heated under reflux for 6 hrs, cooled, quenched into crushed ice, placed at a reduced pressure to remove THF, and filtered to obtain a solid product. The solid was extracted with dichloromethane. The extract was concentrated to 50 mL and a solid precipitated after petroleum ether was added. The precipitate was collected and purified by column chromatography (silica gel-benzene) to obtain 70.0 mg 1-benzyl-3-(5'-hydroxymethyl-2'-furyl)-indazole at a yield of 87%.

mp: 108-109° C.
MS (%), m/z: 304 ($M^+$).
IR (KBr) $\gamma_{max}$: 3350 $cm^{-1}$ (—OH).
$^1$H-NMR (DMSO-$d_6$, 200 MHz) δ: 4.51 (2H, d, J=5.5 Hz, —$CH_2O$—), 5.31 (1H, t, J=5.5 Hz, —OH), 5.70 (2H, s, =$NCH_2$—), 6.48 (1H, d, J=3.4 Hz, H-4'), 6.97 (1H, d, J=3.4 Hz, H-3'), 7.21-7.31 (6H, m, H-5, phenyl), 7.45 (1H, t, J=8.2 Hz, H-6), 7.75 (1H, dd, J=8.2, 1.8 Hz, H-7), 8.12 (1H, dd, J=8.2. 1.0 Hz. C4-H).

EXAMPLE 2

Synthesis of 1-benzyl-3-(5'-methoxycarbonyl-2'-furyl)-6-fluoroindazole (Compound 2)

4'-Fluorophenyl 5-methoxycarbonyl-2-furyl ketone (5.96 g, 24 mmole) was prepared as in Example 1(a), and used as the starting material to obtain 4.1 g 1-benzyl-3-(5'-methoxycarbonyl-2'-furyl)-6-fluoroindazole in a yield of 48.8%, according to the procedure described in Example 1 (b).

mp: 108-109° C.
MS (%), m/z: 350 ($M^+$).
IR (KBr) $\gamma_{max}$: 1710 $cm^{-1}$ (C=O).
$^1$H-NMR (DMSO-$d_6$, 200 MHz) δ: 3.87 (3H, s, —$CH_3$), 5.73 (2H, s, =$NCH_2$—), 7.18-7.37 (7H, m, H-5,3', phenyl), 7.45 (1H, d, J=3.5 Hz, H-4), 7.77 (1H, dd, J=10.0, 1.5 Hz, C7-H), and 8.17 (1H, dd, J=8.0, 6.3 Hz, C4-H).

EXAMPLE 3

Synthesis of 1-benzyl-3-(5'-hydroxymethyl-2'-furyl)-6-fluoroindazole (Compound 3)

1-Benzyl-3-(5'-methoxycarbonyl-2'-furyl)-6-fluoroindazole (93 mg, 0.27 mmole) was used as the starting material and treated according to the procedure described in Example 1 (c) to obtain 75.0 mg 1-benzyl-3-(5'-hydroxymethyl-2'-furyl)-6-fluoroindazole in a yield of 88.0%.

mp: 110-112° C.

MS (%), m/z; 322 (M+).

IR (KBr) $\gamma_{max}$: 3450 cm$^{-1}$ (—OH).

$^1$H-NMR (DMSO-d$_6$, 200 MHz) δ: 4.49 (2H, br, —CH$_2$O—), 5.45 (1H, br, —OH), 5.88 (1H, s, =NCH$_2$—), 6.48 (1H, d, J=3.2 Hz, H-4'), 6.98 (1H, d, J=3.2 Hz, H-3'), 7.10-7.18 (1H, m, H-7), 7.24-7.36 (5H, m, phenyl-H), 7.70 (1H, dd, J=10.0, 2.0 Hz, C5-H), and 8.15 (1H, dd, J=8.5, 5.1 Hz, H-4).

EXAMPLE 4

Synthesis of 1-benzyl-3-(5'-hydroxymethyl-2'-furyl)-6-methylindazole (Compound 7)

1-Benzyl-3-(5'-methoxycarbonyl-2'-furyl)-6-methylindazole (92 mg. 0.27 mmole) was used as the starting material and treated according to the procedure described in Example 1(c) to obtain 74.0 mg 1-benzyl-3-(5'-hydroxymethyl-2'-furyl)-6-methylindazole in a yield of 88%.

mp: 112-114° C.

MS (%), m/z: 318 (M+).

IR (KBr) $\gamma_{max}$: 3400 cm$^{-1}$ (—OH).

$^1$H-NMR (DMSO-d$_6$, 200 MHz) δ: 2.44 (3H, s, —CH$_3$), 4.50 (2H, d. J=5.2 Hz, —CH$_2$O—), 5.30 (1H, br, —OH), 5.64 (2H, s, =6.45 (1H, d, J=3.3 Hz, H-4'), 6.07 (1H, d, J=3.3 Hz, H-3'), 7.08 (1H, dd, J=8.3, 1.0 Hz, H-5), 7.19-7.36 (5H, m, phenyl-H), 7.57 (1H, d, J=1.0 Hz, H-7), and 7.98 (1H, dd, J=8.3, 1.0 Hz, H-4).

EXAMPLE 5

Synthesis of 1-benzyl-3-(5'-hydroxymethyl-2'-furyl)thieno[3,2-c]pyrazole (Compound 6)

(a) Synthesis of 5-methoxycarbonyl-2-furyl 2'-thienyl ketone

2-Thiophenecarbonyl chloride (30.5 g, 0.21 mole), methyl 2-furoate (24 g, 0.19 mole), and anhydrous ferric chloride (0.42 g, 2.6 mmole) were allowed to react following the procedure described in Example 1 to obtain 28.7 g 5-methoxycarbonyl-2-furyl 2'-thienyl ketone in a yield of 63.8%.

mp: 103-106° C.

MS (%), m/z: 236 (M+).

IR (KBr) $\gamma_{max}$: 1720, 1620 cm$^{-1}$ (C=O).

1H-NMR (CDCl$_3$, 200 MHz) δ: 3.98 (3H, s, —CH$_3$), 7.22-7.31 (2H, m, H-3,4), 7.41 (1H, d, J=3.5 Hz, H-4'), 7.76 (1H, d, J=3.5 Hz, H-3'), and 8.36 (1H, d, J=4.5 Hz, H-5).

(b) Synthesis of 1-benzyl-3-(5'-methoxycarbonyl-2'-furyl)thieno[3,2-c]pyrazole

5-Methoxycarbonyl-2-furyl 2'-thienyl ketone (5.7 g, 0.024 mole) was used as the starting material and treated following the same procedure described in Example 1 to obtain 1.2 g 1-benzyl-3-(5'-methoxycarbonyl-2'-furyl)thieno[3,2-c]pyrazole in a yield of 14.8%.

mp: 142-143° C.

MS (%), m/z: 338 (M+).

IR (KBr) $\gamma_{max}$: 1720 cm$^{-1}$ (C=O).

$^1$H-NMR (DMSO-d$_6$, 200 MHz) δ: 3.85 (3H, s, —CH$_3$), 5.62 (2H, s, =NCH$_2$—), 6.92 (1H, d, J=3.5 Hz, H-3'), 7.24 (1H, d, J=4.8 Hz, H-6), 7.26-7.35 (5H, m, phenyl-H), 7.43 (1H, d, J=3.5 Hz, H-4'), and 7.77 (1H, dd, J=4.8, 1.5 Hz, H-5).

(c) Synthesis of the Title Compound

1-Benzyl-3-(5'-methoxycarbonyl-2'-furyl)thieno[3,2-c]pyrazole (90 mg, 0.27 mole) was treated following the procedure described in Example 11 to obtain 63.4 mg 1-benzyl-3-(5'-hydroxymethyl-2'-furyl)thieno[3,2-c]pyrazole in a yield of 69.3%.

mp: 103-104° C.

MS (%),m/z: 310 (M+)

IR (KBr) $\gamma_{max}$: 3360 cm$^{-1}$ (—OH).

$^1$H-NMR (DMSO-d$_6$, 200 MHz) δ: 4.46 (2H, d, J=5.3 Hz, —CH$_2$O—), 5.27 (1H, t, J=5.3 Hz, —OH), 5.55 (2H, s, =NCH$_2$—), 6.43 (1H, d, J=3.2 Hz, H-4'), 6.64 (1H, d, J=3.2 Hz, H-3'), 7.20 (1H, d, J=4.8 Hz, H-6), 7.27-7.35 (5H, m, phenyl-H), and 7.72 (1H, d, J=4.8 Hz, H-5).

EXAMPLE 6

Biological Assays

In Vitro Assays

Approximately 450 ml of blood was obtained from healthy human volunteers and diluted with RPMI 1640 culture medium. A Ficoll gradient (MSL; Eurobio, les Ulis, France) was used to isolate human peripheral blood mononuclear leukocytes (PBMC). The volume ratio of blood, RPMI 1640 culture medium, and MSL was 2:4:1. PBMC were obtained by centrifuging the diluted blood at 500 g at 15° C. for 20 min and washed once with RPMI 1640. The cell pellets were resuspended at a final concentration of 6×10$^6$ cells/ml of the same medium supplemented with 5% heat-inactivated normal human serum (a pool of sera from healthy volunteers) and antibiotics (penicillin 100 UI/ml and streptomycin 100 μg/ml). Aliquots of 500 μl of the cell suspension were dispensed into each well of a 24-well plate and incubated at 37° C. in a 5% CO$_2$-95% air incubator in a humidified atmosphere. To wells were added lipopolysaccharide (LPS, 25 μg/ml) from smooth *E. Coli* 0111:B4 alone or LPS and Compound 1 (10 μM) together. After 24 h, the supernatants were collected, centrifuged at 400 g for 10 min at 15° C. and stored at −20° C. Cytokines were assayed using commercial kits manufactured by R & D Systems (Abingdon, UK). The concentrations of the cytokines were determined using an internal standard according to the manufacturer's instructions.

The results show that Compound 1 inhibited pro-inflammatory cytokine release much more effectively than anti-inflammatory cytoline release. More specifically, Compound 1 exerted more than 80% inhibition of the release of TNF-α and interleukins 1β and 8, and more than 30% inhibition of the release of interleukin-2 and interferon-γ. In contrast, it exerted less than 10% inhibition of the release of anti-inflammatory cytokines (interleukines-4 and 10).

In Vivo Assays:

Mice (25-30 g, ICR strain) were injected intraperitoneally with LPS (60 mg/kg). Most of them were orally treated with Compound 1 (10 mg/kg) in 0.5% carboxymethyl cellulose, and the rest (control mice) were orally treated with vehicle. The control mice died within 27 h after the LPS administration. The mice were euthanatized with intraperitoneal administration of pentobarbital at various time intervals after the LPS administration. Nuclear extracts of lung, spleen, and kidney tissues were prepared by a standard method.

NF-κB DNA binding activity was assessed by an electrophoretic mobility shift assay according to a procedure described in Pan et al., *J Biomed Sci.* 2002, 9: 622-630. Briefly, the nuclear extracts of lung tissues (2 μg) were incubated with a 35-base pair double-stranded $^{32}$P-labeled probe encoding the κB consensus sequence (5'-AGT TGA GGG GAT CCC CCC AGG C-3') in binding buffer (10 mM Tris-HCl, 40 mM NaCl, 10% glycerol, 1 mM EDTA, 1 mM dithiothreitol, 1% Nonidet P-40, 1% deoxycholate, 3 μg/ml polydeoxyinosinic-deoxycytidylic acid) at room temperature for 30 min. The sample was then charged to native 5% polyacrylamide gels and analyzed by autoradiography. For a competition assay, 20-fold molar excess unlabeled consensus oligonucleotide was added 30 min before the labeled probe was added. The components of NF-κB proteins were identified by a supershift assay using antibodies against p65 antibodies.

NF-κB DNA binding activity was also assessed with ELISA-based Trans-AM NF-κB p65 transcription factor assay kits (Active Motif Europe, Rixensart, Belgium) according to the manufacturer's instructions. Tissue extracts of lung, spleen, or kidney tissues (5 μg) were added to 96-well plates coated with an oligonucleotide containing the NF-κB consensus site. Binding of NF-κB to the DNA was visualized by anti-p65 antibodies that specifically recognize activated NF-κB. Specificity of NF-κB activation was determined by competition experiments using NF-κB wild-type and mutant consensus oligonucleotides that were provided with the kit.

The results show that the level of NF-κB/DNA complex increased significantly after LPS was administered, and started to decline 6 hours later, and that treatment with Compound 1 inhibited the increase of the NF-κB/DNA complex level induced by LPS.

Other Embodiments

All of the features disclosed in this specification may be combined in any combination. Each feature disclosed in this specification may be replace by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, a compound structurally analogous to a fused pyrazolyl compound can also be used to practice the present invention. Thus, other embodiments are also within the claims.

What is claimed is:

1. A method for preferentially inhibiting release of four or more pro-inflammatory cytokines over release of one or more anti-inflammatory cytokines in a subject, the method comprising administrating to the subject an effective amount of a compound of the following formula:

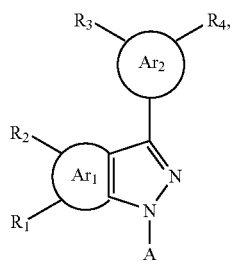

wherein
A is R or

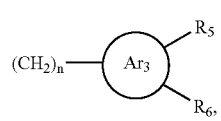

in which R is H, alkyl, aryl, cyclyl, heteroaryl, or heterocyclyl;

$Ar_1$ is thienyl;

$Ar_2$ and $Ar_3$ are independently phenyl, thienyl, furyl, or pyrrolyl;

each of $R_1$, $R_2$, $R_3$, $R_4$, $R_5$, and $R_6$, independently, is R', nitro, halogen, —C(O)—OR', —C(O)—SR', —C(O)—NR'R", —$(CH_2)_m$OR', —$(CH_2)_m$SR', —$(CH_2)_m$NR'R", —$(CH_2)_m$CN, —$(CH_2)_m$C(O)—OR', or —$(CH_2)_m$C(O)H, or $R_1$ and $R_2$ together, $R_3$ and $R_4$ together, or $R_5$ and $R_6$ together are —O$(CH_2)_m$O—, in which each of R' and R", independently, is H, alkyl, cyclyl, aryl, heteroaryl, or heterocyclyl; and m is 0, 1, 2, 3, 4, 5, or 6; and n is 1, 2, or 3.

2. A method for preferentially inhibiting release of four or more pro-inflammatory cytokines over release of one or more anti-inflammatory cytokines in a subject, the method comprising administrating to the subject an effective amount of a compound of the following formula:

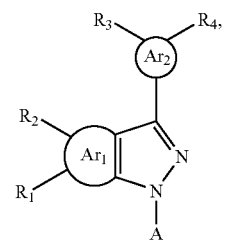

wherein
A is H;

each of $Ar_1$ and $Ar_2$, independently, is phenyl, thienyl, furyl, or pyrrolyl;

each of $R_1$, $R_2$, $R_3$, and $R_4$, independently, is R', nitro, halogen, —C(O)—OR', —C(O)—SR', —C(O)—NR'R", —$(CH_2)_m$OR', —$(CH_2)_m$SR', —$(CH_2)_m$NR'R", —$(CH_2)_m$CN, —$(CH_2)_m$C(O)—OR', or —$(CH_2)_m$C(O)H, or $R_1$ and $R_2$ together, $R_3$ and $R_4$ together, or $R_5$ and $R_6$ together are —O$(CH_2)_m$O—, in which each of R' and R", independently, is H, alkyl, cyclyl, aryl, heteroaryl, or heterocyclyl; and m is 0, 1, 2, 3, 4, 5, or 6; and n is 1, 2, or 3.

3. The method of claim 1, wherein $Ar_2$ is 5'-furyl.

4. The method of claim 3, wherein $R_3$ is $CH_2OH$ and substituted at position 2 of furyl, and $R_4$ is H.

5. A method for preferentially inhibiting release of five or more pro-inflammatory cytokines over release of two anti-inflammatory cytokines in a subject, the method comprising administrating to the subject an effective amount of a compound of the following formula:

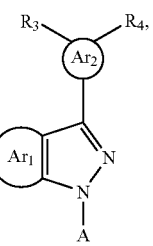

wherein
A is

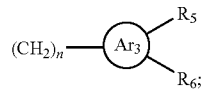

Ar$_1$ is phenyl, thienyl, furyl, or pyrrolyl;
Ar$_2$ is 5'-furyl;
Ar$_3$ is phenyl;
R$_1$ and R$_2$ independently are R', nitro, halogen, —C(O)—OR', —C(O)—SR', —C(O)—NR'R", —(CH$_2$)$_m$OR', —(CH$_2$)$_m$SR', —(CH$_2$)$_m$NR'R", —(CH$_2$)$_m$CN, —(CH$_2$)$_m$C(O)—OR', or —(CH$_2$)$_m$C(O)H;
or R$_1$ and R$_2$ together are —O(CH$_2$)$_m$O—, in which R' and R" independently are H, alkyl, cyclyl, aryl, heteroaryl, or heterocyclyl; and m is 0, 1, 2, 3, 4, 5, or 6;
R$_3$ is CO$_2$H and substituted at position 2 of 5'-furyl;
R$_4$, R$_5$, and R$_6$ are H; and
n is 1.

6. A method for preferentially inhibiting release of five or more pro-inflammatory cytokines over release of two anti-inflammatory cytokines in a subject, the method comprising administrating to the subject an effective amount of a compound of the following formula:

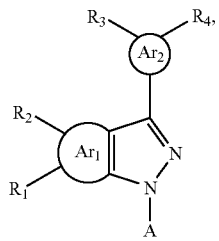

wherein A is H;
Ar$_1$ and Ar$_3$ independently are phenyl, thienyl, furyl, or pyrrolyl;
Ar$_2$ is furyl;
each of R$_1$, R$_2$, R$_3$, R$_4$, R$_5$, and R$_6$, independently, is R', nitro, halogen, —C(O)—OR', —C(O)—SR', —C(O)—NR'R", —(CH$_2$)$_m$OR', —(CH$_2$)$_m$SR', —(CH$_2$)$_m$NR'R", —(CH$_2$)$_m$CN, —(CH$_2$)$_m$C(O)—OR', or —(CH$_2$)$_m$C(O)H, or R$_1$ and R$_2$ together, R$_3$ and R$_4$ together, or R$_5$ and R$_6$ together are —O(CH$_2$)$_m$O—, in which each of R' and R", independently, is H, alkyl, cyclyl, aryl, heteroaryl, or heterocyclyl; and m is 0, 1, 2, 3, 4, 5, or 6; and
n is 1, 2, or 3.

7. The method of claim 6, wherein R$_3$ is CO$_2$CH$_3$ and substituted at position 2 of furyl, and R$_4$ is H.

8. The method of claim 1, wherein the five pro-infammatory cytokines are interleukin 1 β, interleukin 6, interleukin 8, interferon γ and TNF-α;
and the two anti-inflammatory cytokines are interleukin 4 and interleukin 10.

9. A method for preferentially inhibiting release of five or more pro-inflammatory cytokines over release of two anti-inflammatory cytokines in a subject, the method comprising administrating to the subject an effective amount of Compound 2

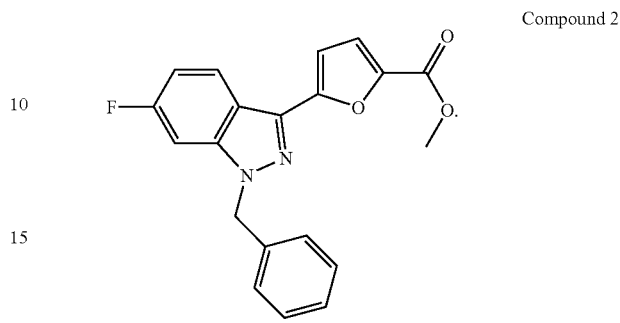

Compound 2

10. The method of claim 1, wherein said compound is

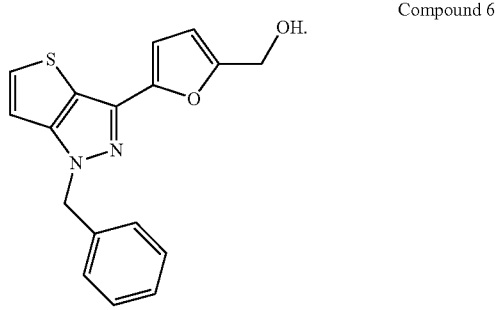

Compound 6

11. A method for preferentially inhibiting release of five or more pro-inflammatory cytokines over release of two anti-inflammatory cytokines in a subject, the method comprising administrating to the subject an effective amount of Compound 7

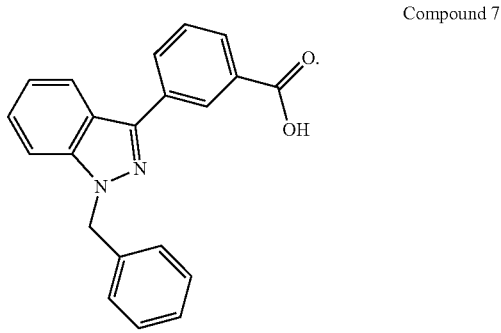

Compound 7

* * * * *